US012590058B2

(12) United States Patent
Bonrath et al.

(10) Patent No.: US 12,590,058 B2
(45) Date of Patent: Mar. 31, 2026

(54) PHOTOOXIDATION OF 2,4,6-TRIMETHYLPHENOL

(71) Applicants: DSM IP ASSETS B.V., Heerlen (NL); UNIVERSITÄT BASEL, Basel (CH)

(72) Inventors: Werner Bonrath, Kaiseraugst (CH); Thomas Buchholz, Kaiseraugst (CH); Thomas Netscher, Kaiseraugst (CH); Jan Schuetz, Kaiseraugst (CH); Christof Sparr, Kaiseraugst (CH)

(73) Assignees: DSM IP ASSETS B.V., Maastricht (NL); UNIVERSITÄT BASEL, Basel (CH)

( * ) Notice: Subject to any disclaimer, the term of this patent is extended or adjusted under 35 U.S.C. 154(b) by 498 days.

(21) Appl. No.: 18/256,992

(22) PCT Filed: Dec. 13, 2021

(86) PCT No.: PCT/EP2021/085379

§ 371 (c)(1),
(2) Date: Jun. 12, 2023

(87) PCT Pub. No.: WO2022/128852

PCT Pub. Date: Jun. 23, 2022

(65) Prior Publication Data

US 2024/0059650 A1 Feb. 22, 2024

(30) Foreign Application Priority Data

Dec. 15, 2020 (EP) .................................... 20214213

(51) Int. Cl.
*C07C 407/00* (2006.01)
*C07C 37/08* (2006.01)

(52) U.S. Cl.
CPC ........ *C07C 407/00* (2013.01); *C07C 2601/16* (2017.05)

(58) Field of Classification Search
CPC .............................. C07C 407/00; C07C 37/08
See application file for complete search history.

(56) References Cited

U.S. PATENT DOCUMENTS 3,966,818 A 6/1976 Ichikawa et al.
4,164,516 A * 8/1979 Costantini ............... C07C 45/39 568/360

FOREIGN PATENT DOCUMENTS

JP 2015-1688667 9/2015

OTHER PUBLICATIONS

Nardello V et al., "Singlet oxygen generation from H202/Mo042: peroxidation of hydrophobic substrates in pure organic solvents", Tetrahedron Letters, Nov. 25, 2002, pp. 8731-8734, vol. 43, No. 48.
International Search Report for PCT/EP2021/085379, mailed Mar. 11, 2022, 2 pages.
Written Opinion of the ISA for PCT/EP2021/085379, mailed Mar. 11, 2022, 5 pages.
The First Office Action, CN Application No. 202180083673.6, Dec. 9, 2024.
Wei Liu et al, "Hypocrellin B Graft on Activated Carbon and Photo-catalytic Oxidation of 2,3,5-trimethylphenol", Proc. of SPIE, vol. 7280, 728015 (2009).

* cited by examiner

*Primary Examiner* — Sikarl A Witherspoon
(74) *Attorney, Agent, or Firm* — NIXON & VANDERYE P.C.

(57) ABSTRACT

The present invention relates to the photooxidation of 2,4,6-trimethyl-phenol to yield 4-hydroperoxy-2,4,6-trimethyl-cyclohexa-2,5-dien-1-one using methylene blue as photo-sensitizer in a solvent mixture of water and alcohols using light of the high wavelength range of the visible spectrum. This process allows 5 obtaining 4-hydroxy-2,4,6-trimethyl-cyclohexa-2,5-dien-1-one and 2,3,5-trimethyl-hydroquinone in high yields and selectivity from 2,4,6-trimethylphenol.

22 Claims, 10 Drawing Sheets

PHOTOOXIDATION OF 2,4,6-TRIMETHYLPHENOL

Figure 1A:
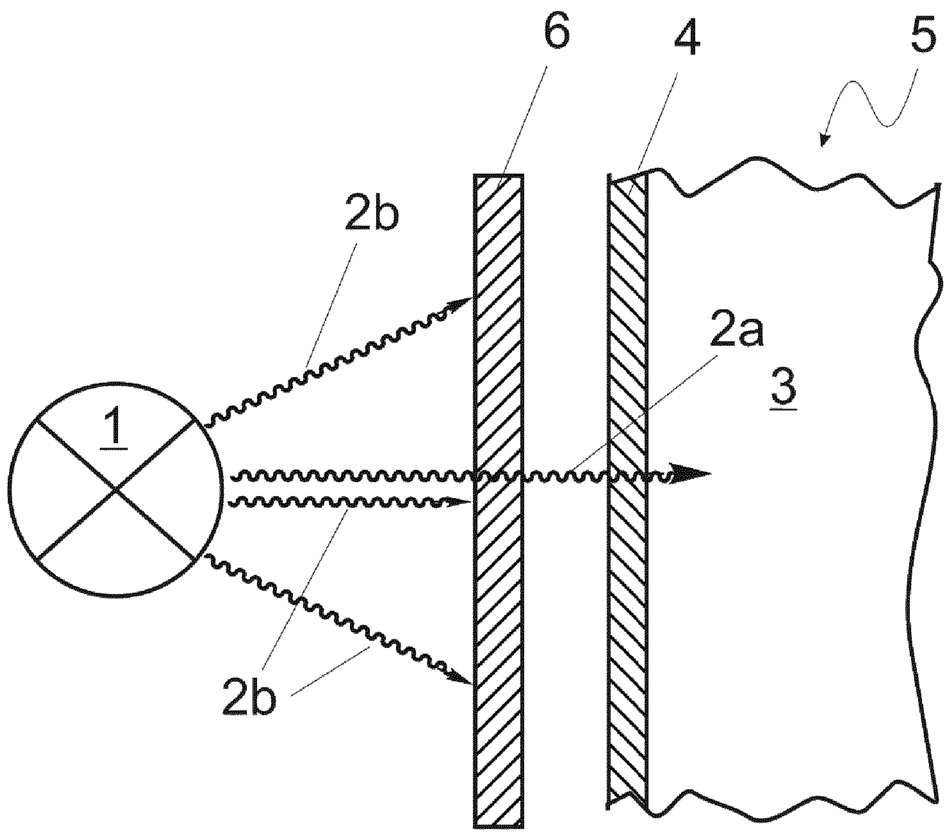

This application is the U.S. national phase of International Application No. PCT/EP2021/085379 filed Dec. 13, 2021, which designated the U.S. and claims priority to EP patent application No. 20214213.9 filed Dec. 15, 2020, the entire contents of each of which are hereby incorporated by reference.

TECHNICAL FIELD

The present invention relates to preparation of 4-hydroperoxy-2,4,6-trimethylcyclohexa-2,5-dien-1-one and 2,3,5-trimethylhydroquinone and particularly to the field of photooxidation of 2,4,6-trimethylphenol (=mesitol).

BACKGROUND OF THE INVENTION 2,3,5-Trimethylhydroquinone is a key intermediate in the production of alpha-tocopherol.

T. Netscher discloses in *Vitam. Horm.* 2007, 76, 155-202, particular on page 159, and W. Bonrath et al. in *Angew. Chem. Int. Ed.* 2012, 51, 12960-12990, particularly on page 12983, that 2,3,5-trimethylhydroquinone can be obtained from m-cresol which is catalytically methylated to 2,3,6-trimethylphenol which is then transformed by oxidation to 2,3,5-trimethyl-benzoquinone and subsequently reduced to 2,3,5-trimethylhydroquinone. Alternative processes start from isophorones using oxidation/hydrogenation/isomerization sequences. A further process is using mesitol as starting product using oxidation and rearrangement to yield 2,3,5-trimethylhydroquinone.

US 2012/0203013 A1 discloses the oxidation of 2,4,6-trimethylphenol (mesitol) by hydrogen peroxide in the presence of a bismuth catalyst. M. C. Carreño et al. discloses in *Angew. Chem. Int. Ed.* 2006, 45, 2737-2741 that the oxidation of mesitol can be performed by oxone in acetonitrile.

It has been proposed by Murtinho D. et al., *J. Chem. Soc. Perkin Trans.* 2, 2000, 2441-2447 to photooxidize 2,3,5-trimethylphenol to obtain 2,3,5-trimethyl-benzoquinone using oxygen in the presence of a photosensitizer. In particular, it discloses methylene blue as photosensitizer for 1,5-dihydroxynaphthalene in a mixture of acetonitrile and dichloromethane. However, as a result of moderate yield of 78 to 82%, it has been suggested using porphyrin type photosensitizers instead. Such porphyrin compounds are rather expensive and not readily commercially available. On the other hand acetonitrile as well as dichloromethane are solvents which have significant ecological and ecotoxicological disadvantages. Furthermore, it is known that it is much more difficult to oxidize phenols than naphthols.

In contrast to 2,3,5-trimethylphenol, mesitol (=2,4,6-trimethylphenol) is readily available. It is commercially very interesting to offer a process for the manufacturing of 2,3,5-trimethylhydroquinone starting from mesitol instead of m-cresol or 2,3,5-trimethylphenol, respectively.

SUMMARY OF THE INVENTION

Therefore, the problem to be solved by the present invention is to offer an efficient method of synthesizing 4-hydroperoxy-2,4,6-trimethylcyclohexa-2,5-dien-1-one or 4-hydroxy-2,4,6-trimethylcyclohexa-2,5-dien-1-one or 2,3,5-trimethylhydroquinone, respectively, in high yield and selectivity.

It has been found that the photooxidation according to claim 1 or the process according to claim 12 or 14, respectively, offers an efficient way of solving this problem.

In the present invention methylene blue can be used, which is a readily available and cost-effective and very attractive photosensitizer and get the desired product not only in very high yield at high conversion but also in a very high selectivity. Particularly advantageous is that the process can be performed in the absence of any chlorinated solvents. Hence, said process is highly attractive for industrial application.

Further aspects of the invention are subject of further independent claims. Particularly preferred embodiments are subject of dependent claims.

DETAILED DESCRIPTION OF THE INVENTION

The present invention relates in a first aspect to a process of manufacturing the compound of the formula (I) from the compound of the formula (II) by photooxidation (I)

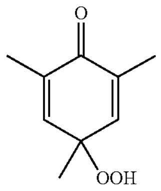

(II)

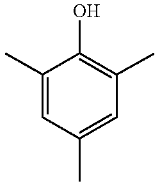

using oxygen and a photosensitizer of the formula (III)

(III)

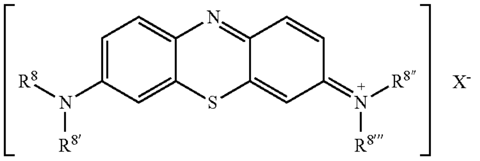

wherein $R^8$, $R^{8'}$, $R^{8''}$ and $R^{8'''}$ independently from each other represent either a H, or a $C_{1-4}$ alkyl group;

or wherein $R^8$ and $R^{8'}$ and/or $R^{8''}$ and $R^{8'''}$ form together with N a five or six membered ring;

with the proviso that at least one of the residues $R^8$, $R^{8'}$, $R^{8''}$ and $R^{8'''}$ is different from H;

and $X^-$ represents an anion;

in solvent mixture of water and at least one $C_{1-8}$ alkanol or at least one $C_{2-4}$ alkylene diol;

and using light which has a peak wavelength ($\lambda_{max}$) in its spectrum in the range of between 580 and 780 nm.

For sake of clarity, some terms as used in the present document are defined as follows:

In the present document, a "$C_{x-y}$-alkyl" group is an alkyl group comprising x to y carbon atoms, i.e., for example, a $C_{1-3}$-alkyl group is an alkyl group comprising 1 to 3 carbon atoms. The alkyl group can be linear or branched. For example —$CH(CH_3)$—$CH_2$—$CH_3$ is considered as a $C_4$-alkyl group.

Analogously, a $C_{x-y}$ alkanol, respectively a $C_{x-y}$ alkylene diol, is an alcohol having one, respectively two, OH groups where the alcohol has an alkyl respectively alkylene group comprising x to y carbon atoms.

In case identical labels for symbols or groups are present in several formulae, in the present document, the definition of said group or symbol made in the context of one specific formula applies also to other formulae which comprises the same said label.

The peak wavelength is the wavelength where the spectrum reaches its highest intensity.

In the said process 2,4,6-trimethylphenol (=compound of the formula (II), mesitol) is photooxidized to yield 4-hydroperoxy-2,4,6-trimethylcyclohexa-2,5-dien-1-one (=compound of the formula (I)).

Mesitol is a known chemical and is commercially available in large quantities from different suppliers and can be easily produced for example by the reaction of mesitylene with peroxymonophosphoric acid.

In the photooxidation a photosensitizer of the formula (III) is used (III)

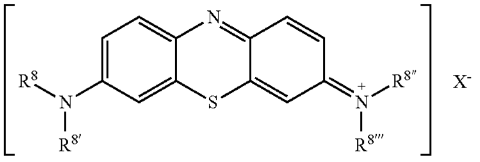

wherein $R^{8}$, $R^{8'}$, $R^{8''}$ and $R^{8'''}$ independently from each other represent either a H, or a $C_{1-4}$ alkyl group;

or wherein $R^{8}$ and $R^{8'}$ and/or $R^{8''}$ and $R^{8'''}$ form together with N a five or six membered ring;

with the proviso that at least one of the residues $R^{8}$, $R^{8'}$, $R^{8''}$ and $R^{8'''}$ is different from H;

and $X^-$ represents an anion.

In one embodiment, $R^{8}$ and $R^{8'}$ and/or $R^{8''}$ and $R^{8'''}$ form together —$(CH_2)_5$— or —$(CH_2)_2$—NH—$(CH_2)_2$— or —$(CH_2)_2$—N($C_{1-4}$ alkyl)-$(CH_2)_2$— or —$(CH_2)_2$—S—$(CH_2)_2$— or —$(CH_2)_2$—O—$(CH_2)_2$—.

It is further preferred that $R^{8}$=$R^{8''}$ and/or $R^{8'}$=$R^{8'''}$. More preferred is that $R^{8}$=$R^{8'}$=$R^{8''}$=$R^{8'''}$.

More preferably, the substituent $R^{8}$, $R^{8'}$, $R^{8''}$ and $R^{8'''}$ represent a $C_{1-4}$ alkyl group, even more preferably $R^{8}$=$R^{8'}$=$R^{8''}$=$R^{8'''}$=methyl or ethyl.

Most preferably $R^{8}$=$R^{8'}$=$R^{8''}$=$R^{8'''}$=$CH_3$.

In formula (III) $X^-$ represents an anion. The role of the anion is to counter balance the charge of the cation which is represented in the above formula by the part within the brackets ([)(]). Therefore, in principle any anion can be used.

Preferably, $X^-$ represents a halide, most preferably a chloride.

Preferably, the compound of the formula (III) is methylene blue. Further preferred is the compound of the formula (III) in the form of a double salt with zinc chloride, particularly a double salt of methylene blue with zinc chloride or in the form of a hydrate, preferably methylene blue hydrate (CAS:122965-43-9).

It has been found that the photosensitizer of the formula (III) is particularly suited in the photooxidation of the compound of the formula (II).

It is essential that for the above photooxidation light is used which has a peak wavelength ($\lambda_{max}$) in its spectrum in the range of between 580 and 780 nm.

In one preferred embodiment light is used which has a peak wavelength ($\lambda_{max}$) in its spectrum in the range of between 585 and 625 nm. This corresponds to a light which is perceived as orange.

In another, more preferred, embodiment light is used which has a peak wavelength ($\lambda_{max}$) in its spectrum in the range of between 625 and 740 nm. This corresponds to a light which is perceived as red.

This light is mainly of the high wavelength range of the visible spectrum.

In a further preferred embodiment the light used is characterized so that more than 80% of the light has a wavelength of between 525 and 780 nm, preferably more than 80% of the light has a wavelength of between 525 and 700 nm, more preferably more than 65% of the emitted light has a wavelength of between 550 and 650 nm.

In an even further preferred embodiment the light used is characterized so that more than 80% of the light has a wavelength of between 550 and 780 nm, preferably more than 80% of the light has a wavelength of between 600 and 760 nm, more preferably more than 65% of the emitted light has a wavelength of between 625 and 700 nm, most preferably more than 85% of the emitted light has a wavelength of between 625 and 700 nm.

It is, therefore, important that the light used has no significant amount of light having a wavelength below 580 nm in its spectrum. It is essential that light of the colours green, blue and violet or colours having significant amounts green, blue and violet in their spectrum have been found not to be suited for the above photooxidation.

In one embodiment, the light which is used for the photooxidation can be realized by filtering the undesired light wavelengths from a light source. For example a light source having a multichromatic or white emission can be filtered by a filter which blocks off the undesired wavelength.

There are different possibilities of such filters known and commercially available such as absorption, dichroic, monochromatic, band-pass, short-pass or wedge filters, using different physical methods for filtration of light.

Particularly useful are absorption or cut-off filters.

It is particularly preferred that the light source is a white LED lamp in combination with a filter blocking wavelengths below 500 nm, most particularly below 625 nm.

A red LED lamp is the most preferred light source for the light.

FIG. 1*a* represents a schematic representation of this embodiment. The light source (1) emits radiation of different wavelengths, which have the desired wavelengths (2*a*) and undesired wavelengths (2*b*). The light source is preferably a white light, more preferably a white LED. A filter (6) is positioned between light source (1) and the photoreactor which has a transparent wall (4). The filter (6) filters the light of undesired wavelengths to provide a light which has a peak wavelength ($\lambda_{max}$) in its spectrum in the range of between 580 and 780 nm. The filter (6) is preferably an "orange filter" or "red filter", i.e. a filter that allows only light with a wavelength of between 585 and 625 nm or between 625 and 740 nm to pass through. The reaction mixture (3), which comprises at least oxygen and the compound of the formula (II) and the solvent mixture of water and at least one $C_{1-8}$ alkanol or at least one $C_{2-4}$ alkylene diol, is inside the photoreactor (5).

By the photoreaction a compound of the formula (I) is produced by photochemical reaction from compound of the formula (II) and oxygen, particular in a gas mixture comprising at least 20% by volume of oxygen.

A specific preferred example of this embodiment is a white LED. The light of which is filtered in such a way that all light which is not of the desired wavelengths is blocked or at least significantly absorbed (e.g. using a "orange filter" (allowing transmission of light only of between 585 and 625 nm) or "red filter" (allowing transmission of light only of between 625 and 740 nm)).

So, the light source for the light is preferably a white LED lamp in combination with a filter blocking wavelengths below 500 nm, particularly below 625 nm.

In a further embodiment, the light which is used for the photooxidation can be produced by a respective light source emitting light of the desired wavelengths.

Figure 1B:
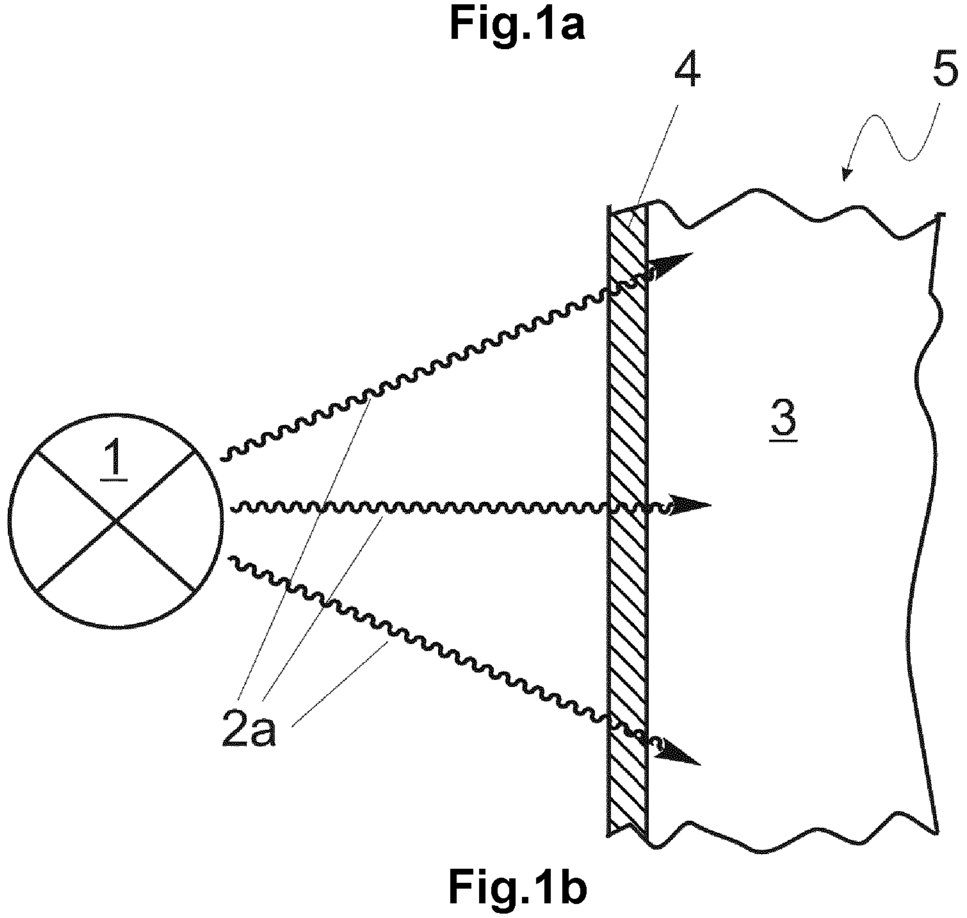

FIG. 1*b* represents a schematic representation of this embodiment. The light source (1) emits radiation of the desired wavelengths (2*a*) to provide a light which has a peak wavelength ($\lambda_{max}$) in its spectrum in the range of between 580 and 780 nm. The light source is preferably an orange or red light, more preferably an orange or red LED to provide a light using light which has a peak wavelength ($\lambda_{max}$) in its spectrum in the range of between 580 and 780 nm.

The reaction mixture (3), which comprises at least oxygen and the compound of the formula (II) and the solvent mixture of water and at least one $C_{1-8}$ alkanol or at least one $C_{2-4}$ alkylene diol, is inside the photoreactor (5). By the photoreaction a compound of the formula (I) is produced by photochemical reaction from compound of the formula (II) and oxygen.

Specific examples of light sources of this embodiments are red LEDs or red or orange Lasers, preferably red or orange LED lamps. Red and orange LED lamps are commercially broadly available. Red and orange LEDs can provide high intensities of red or orange light. In a preferred embodiments a flexible strip having a plurality of individual LEDs incorporated in said strip. This allows to assure radial orientation of the LED around a curved surface such as a transparent tube, for example, by simply wrapping, preferably in a helical manner, said strip around the tube.

The photooxidation is performed in a solvent mixture of water and at least one $C_{1-8}$ alkanol or at least one $C_{2-4}$ alkylene diol.

The $C_{1-8}$ alkanol is preferably selected from the group consisting of methanol, ethanol, propanol, isopropanol, butanol, heptanol and hexanol, more preferably selected from the group consisting of methanol, ethanol and isopropanol.

The $C_{2-4}$ alkylene diol is preferably selected from the group consisting of ethane-1,2-diol, propane-1,2-diol, propane-1,3-diol, butane-1,3-diol, butane-1,4-diol, butan-1,2-diol and butane-2,3-diol, preferably selected from the group consisting of ethane-1,2-diol, propane-1,2-diol and propane-1,3-diol.

It is preferred that the solvent mixture is a mixture of water and at least one $C_{1-8}$ alkanol or at least one $C_{2-4}$ alkylene diol form a homogeneous phase.

It is preferred that the solvent mixture is a mixture of water and at least one $C_{1-8}$ alkanol or at least one $C_{2-4}$ alkylene diol. More preferred the solvent mixture is a mixture of water and $C_{1-8}$ alkanol.

Even more preferred the solvent mixture is a mixture of water and $C_{1-6}$ alkanol.

More preferably the solvent mixture is a mixture of water and methanol and/or ethanol and/or isopropanol. Most preferably, the solvent mixture is a mixture of water and methanol and/or ethanol.

It is preferred that the volume ratio of water to the sum of $C_{1-8}$ alkanol and $C_{2-4}$ alkylene diol is in the range of between 1:10 and 1:1, particularly between 1:5 and 1:2.

In a very preferred embodiment the solvent mixture is a mixture of water and methanol, preferably in a volume of water to methanol in the range of 1:20 to 1:2, preferably of 1:10 and 1:2, more preferably of 1:6 and 1:3.ratio, most preferably 1:4.

It is a key advantage of the present invention that the photooxidation is made in a solvent mixture consisting of water and at least one $C_{1-8}$ alkanol or at least one $C_{2-4}$ alkylene diol, which are ecologically and ecotoxicologically all very favourable solvents and are also economically advantageous. Hence, it is very favourable that the above process is performed in the absence of any chlorinated solvent.

It is preferred that the concentration of the compound of the formula (II) is in the range of between 0.002 to 2.0 mol/l, preferably 0.01 to 0.2 mol/l at the beginning of the photooxidation.

Further preferred is that the ratio of the compound of the formula (III) to the compound of the formula (II) is in the range of between 0.005 and 20 mol %, preferably between 0.05 and 20 mol %, more preferably between 0.2 and 10 mol %.

In one embodiment oxygen is used in a form of a mixture comprising oxygen and an inert gas. It is preferred that the amount of oxygen in such a mixture comprising oxygen and an inert gas is at least 15% by volume, particularly at least 20% by volume. Such a mixture may, for example, be a binary mixture such as a mixture oxygen/nitrogen or oxygen/argon or alike. Said mixture can consist of or comprise two or more inert gases. It is particularly preferred to use air as such a mixture comprising oxygen and an inert gas.

In a preferred embodiment, oxygen is used in a substantially pure form, i.e. that the amount of oxygen in the gas is 90%-100%, more preferably 95%-100%, even more preferably 99%-100%.

The photooxidation can take place at ambient pressure or under pressure. It is preferred that the oxidation takes place under pressure, particularly under a pressure of more than 2 bar, preferably more than 3 bar, more preferably under a pressure of between 2 and 20 bar.

The photooxidation is performed in a suitable photoreactor. A preferred photoreactor is a flow reactor, particularly in a spiral flow reactor.

The individual components can be introduced separately or as mixture into the photoreactor. Preferably the reaction mixture is prepared before entering into the photoreactor.

In one of the preferred embodiments, an oxygen containing solvent mixture is admixed to compound of the formula (II) before entering into the photoreactor.

In another preferred embodiment, the solvent mixture is admixed to compound of the formula (II) which already contains oxygen before entering into the photoreactor.

In most preferred embodiments, oxygen is added to a pre-mixture which at least comprises compound of the formula (II) and the solvent mixture.

The reaction preferably is processed in such a manner that the pressure of oxygen is controlled by suitable valves and mass flow controller. Such process control equipment and methods for photoreactions using liquids and gases is known by the person skilled in the art.

It is preferred that the photooxidation is made in a reactor allowing a continuous process, as it is preferred that said process is a continuous process.

4-hydroperoxy-2,4,6-trimethylcyclohexa-2,5-dien-1-one (compound of formula (I)) can be obtained in very high yield, preferably more than 95%, even more preferably more than 98%, and very high selectivity by this photooxidation process (step a)).

In a further aspect the present invention relates to a process of preparing compound of the formula (IV) from compound of the formula (II) comprising the steps a) photooxidation of compound (II) as described above in great details to yield the compound of the formula (I);

(I)

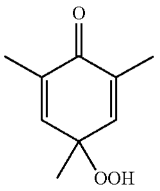

(II)

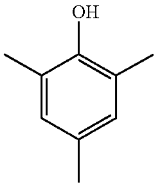

b) reduction of the compound of the formula (I) by means of a reducing agent, to yield the compound of the formula (IV)

(I)

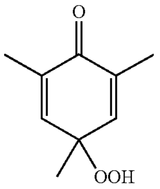

(IV)

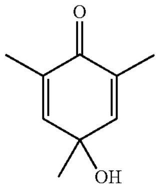

For the reduction of the compound of the formula (I) in step b) several reducing agents can be used.

Suitable as reducing agents can be thiosulphates, trialkylamines, tertiary phosphine, hydrogen, dithionates, sulfites, trialkylphosphites, iodides, metals or dialkylsulfides.

The reducing agent is preferably selected from the group consisting of $Na_2S_2O_3$ (sodium thiosulphate), $NEt_3$ (triethylamine), $PPh_3$, (triphenylphosphine), $H_2$/PdC, $Na_2S_2O_4$ (sodium dithionate), $Na_2SO_3$ (sodium sulfite), $P(OEt)_3$ (triethyl phosphite), NaI (sodium iodide), Zn (and/or other metals) and DMS (dimethyl sulfide).

Preferred as reducing agents are thiosulphate, particularly sodium thiosulphate.

It is preferred that the reducing agent is used in a significant molecular excess, most preferably in an amount of between 2 to 10 equivalents relative to compound of the formula (I). It is further preferred that the reduction is made in a aqueous alcohol particularly at room temperature.

The reduction is indicated by a colour change to pink.

The reduction of 4-hydroperoxy-2,4,6-trimethylcyclohexa-2,5-dien-1-one (compound of formula (I)) is performed in quantitative scale and yield in 4-hydroxy-2,4,6-trimethylcyclohexa-2,5-dien-1-one (compound of formula (IV)) of more than 90%, preferably more than 92%, can be obtained.

The reduction in step b) can be performed in a batch-process or in a continuous process.

It is preferred that the step b) is performed in a continuous way.

For example, the adding of the reducing agent can be performed at the end of the photoreactor as described above. It is, furthermore, preferred that the reduction of step b) is performed in a flow reactor.

Figure 4A:
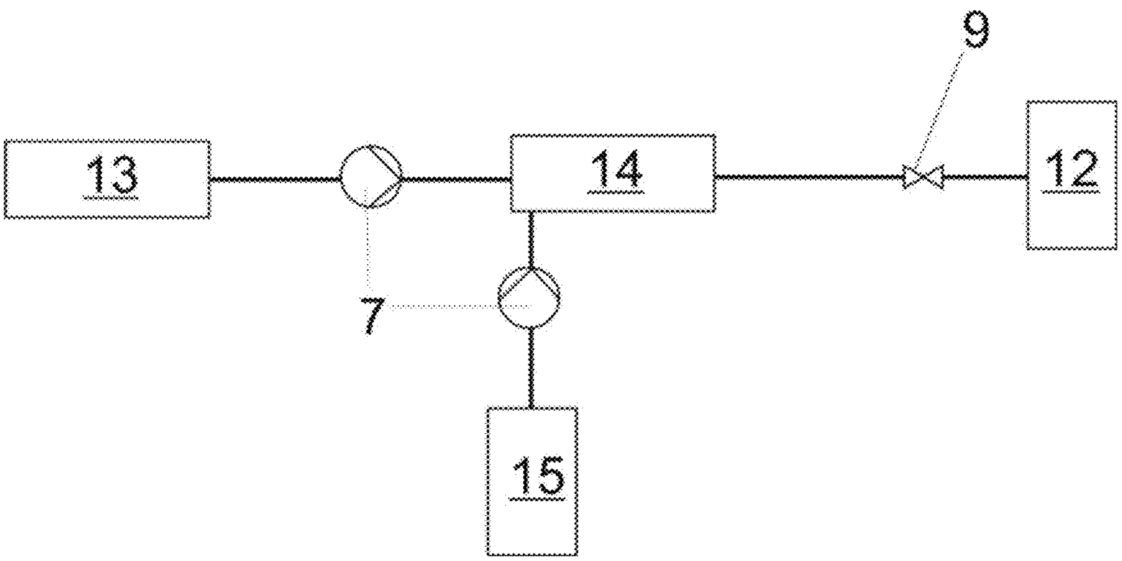
Figure 4B:
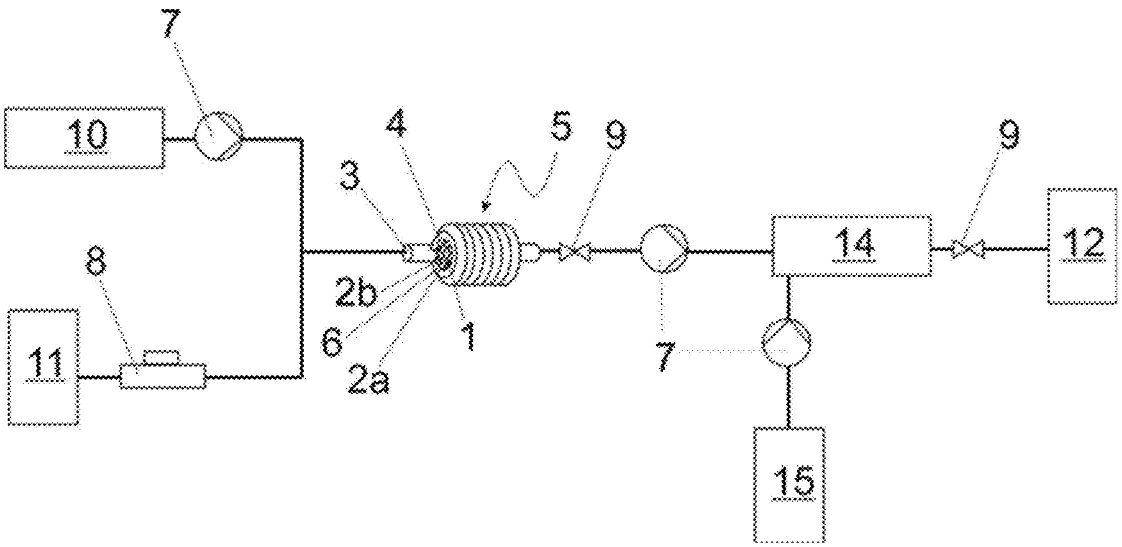

FIG. 4*a* and FIG. 4*b* show more details for these embodiments.

In a further aspect the present invention relates to a process of preparing compound of the formula (IV) from compound of the formula (II) comprising the steps a) photooxidation of compound (II) as described above in great details to yield the compound of the formula (I);

(I)

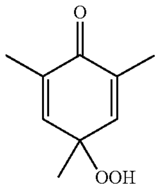

(II)

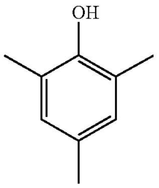

b) reduction of the compound of the formula (I) by means of a reducing agent to yield the compound of the formula (IV)

(I)

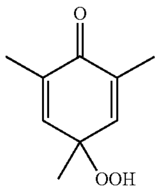

-continued (IV)

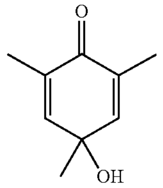

c) treatment of compound of the formula (IV) with a basic substance at a temperature of >200° C., preferably >240° C., to yield the compound of the formula (V)

(IV)

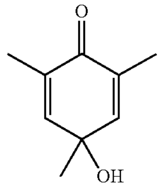

(V)

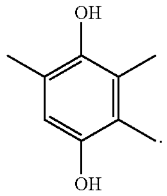

Figure 6:
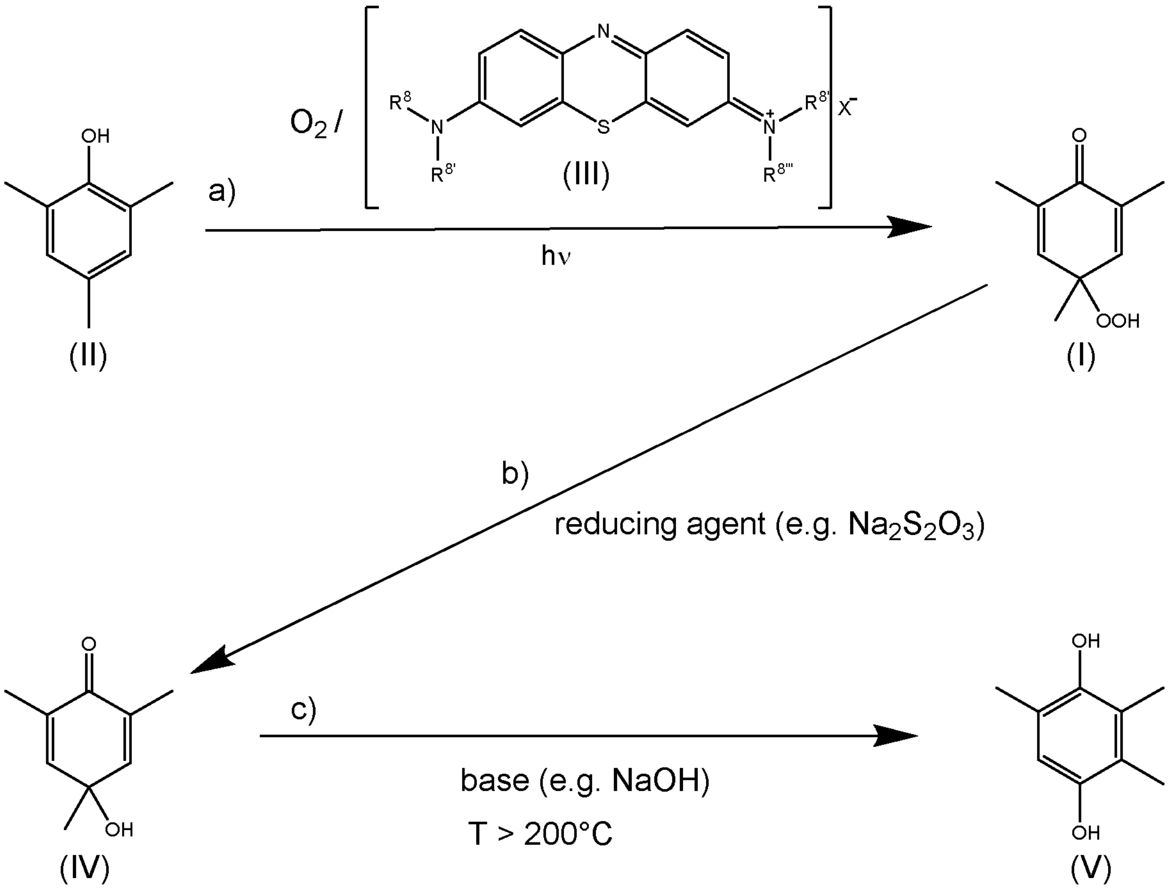

The steps a) and b) have been already discussed above in great detail. FIG. 6 shows schematically the reaction sequence of the steps a), b) and c).

In step c) the compound of the formula (IV) is treated with a basic substance at a temperature of >200° C., preferably >240° C., to yield the compound of the formula (V).

Usable as this basic substance are particularly the alkali metals such, for example, as sodium, potassium, lithium, rubidium and caesium; the alkaline earth metals such, for example, as calcium, magnesium, barium, and strontium; as well as the basic compounds containing at least one of these metals in their molecular structure. The following compounds are mentioned as examples for such basic substances:

A. The hydroxides of alkali metals or alkaline earth metals such, for example, as sodium hydroxide, potassium hydroxide, lithium hydroxide, calcium hydroxide, magnesium hydroxide and barium hydroxide; and B. The carbonates and bicarbonates of alkali metals or alkaline earth metals such, for example, as sodium carbonate, sodium bicarbonate, potassium carbonate, potassium bicarbonate, calcium carbonate, barium carbonate and magnesium carbonate; and C. The oxides of alkaline earth metals such, for example, as calcium oxide, magnesium oxide and barium oxide; and D. The alkali metal- or alkaline earth metal-containing compounds that have hitherto been used as buffers such, for example, as a suitable mixture of an alkali dihydrogen phosphate such as monopotassium dihydrogen phosphate and a dialkali monohydrogen phosphate such as dipotassium monohydrogen phosphate, or the alkali metal salts of such organic carboxylic acids as boric acid, citric acid, lactic acid, tartaric acid and acetic acid.

It is preferred that step c) is performed in the presence of water. It is further preferred that next to water at least one water-soluble alcohol, preferably methanol and/or ethanol and/or iso-propanol, is present in step c).

The step c) is preferably carried out in the presence of the basic substance so that pH is not less than 6.5, and preferably not less than 7. A most preferred pH of the reaction mixture is 7-14.

It is preferred that the step c) is performed under reducing conditions or under inert atmosphere, particularly under nitrogen or argon. Step c) is preferably carried out in the presence of a reducing substance. Examples of such reducing substance are sodium sulphite ($Na_2SO_3$), sodium bisulphite ($NaHSO_3$), sodium dithionite ($Na_2S_2O_4$), and sodium thiosulfate ($Na_2S_2O_3$).

Preferably the basic reaction mixture is neutralize at the end of the reaction by means of an acid.

Preferably, the reaction step c) is performed as disclosed in U.S. Pat. No. 3,957,887, particularly as described in its example 12.

The reaction of step c) can be performed in a batch-process or in a continuous process.

It is preferred that the step c) is performed in a continuous way.

Step c) can take place simultaneously with or after step b). In other words, the intermediate formed in step b) can directly react further to the compound of the formula (V) using suitable conditions in the reduction step b). It is, however, preferred that step c) is performed after step b) has taken place, preferably completely taken place.

It is preferred that step c) takes place in a flow reactor.

It is preferred that step c) is performed in a flow reactor which place after the flow reactor in which step b) is performed. In another embodiment, the reaction of step b) is taken place at the downstream end of a continuous reactor in which the reaction step b) is taken place.

In an even further embodiment, the reaction steps a) and b) and c) are performed all in one flow reactor in which first the photooxidation (step a)), then downstream the reduction of step b) and further downstream the reaction step is taken place.

Figure 5A:
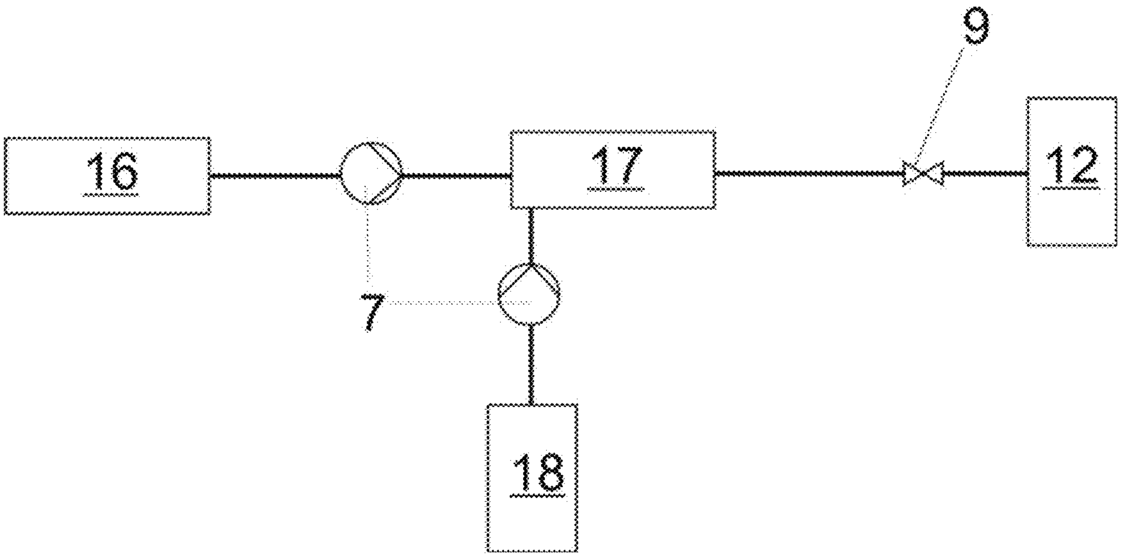
Figure 5B:
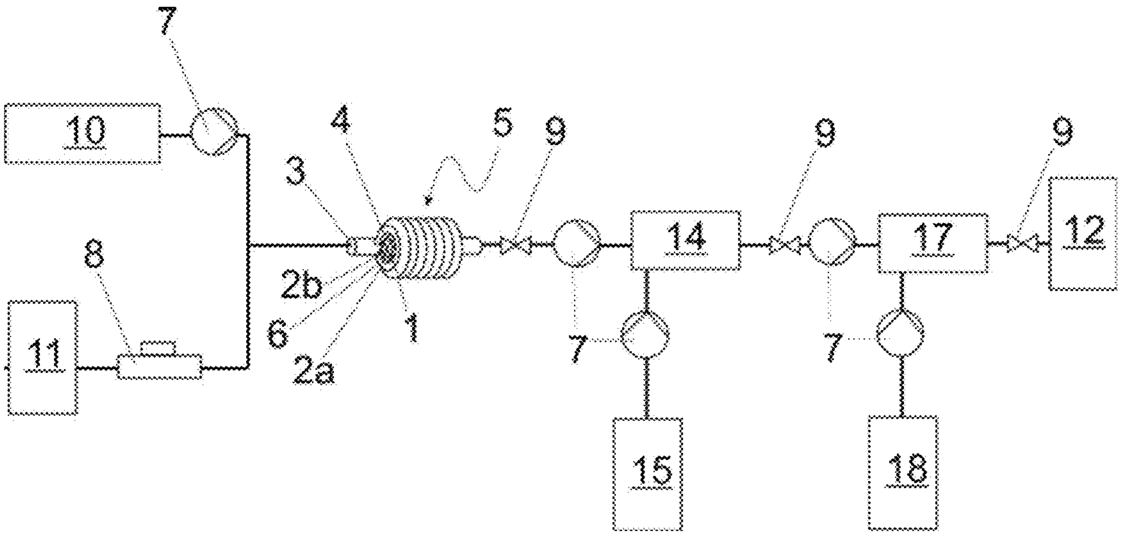

FIG. 5*a* and FIG. 5*b* and FIG. 5*c* show more details for these embodiments.

The present invention shows that 4-hydroperoxy-2,4,6-trimethylcyclohexa-2,5-dien-1-one or 4-hydroxy-2,4,6-trimethylcyclohexa-2,5-dien-1-one or 2,3,5-trimethylhydroquinone, respectively, can be obtained in high yield and selectivity. Particularly, it could be shown that these substances can be obtained in processes all based on mesitol in high yield and selectivity. It could be shown that by this process 2,3,5-trimethylhydroquinone can be obtained from mesitol by an overall yield (step a), b) c)) of more than 84%.

FIGURES

FIG. 1*a* shows a schematic representation of a photooxidation using a light source and a filter to produce a light with a peak wavelength ($\lambda_{max}$) in its spectrum in the range of between 580 and 780 nm.

FIG. 1*b* shows a schematic representation of a photooxidation using a light source with a peak wavelength ($\lambda_{max}$) in its spectrum in the range of between 580 and 780 nm.

Figure 2A:
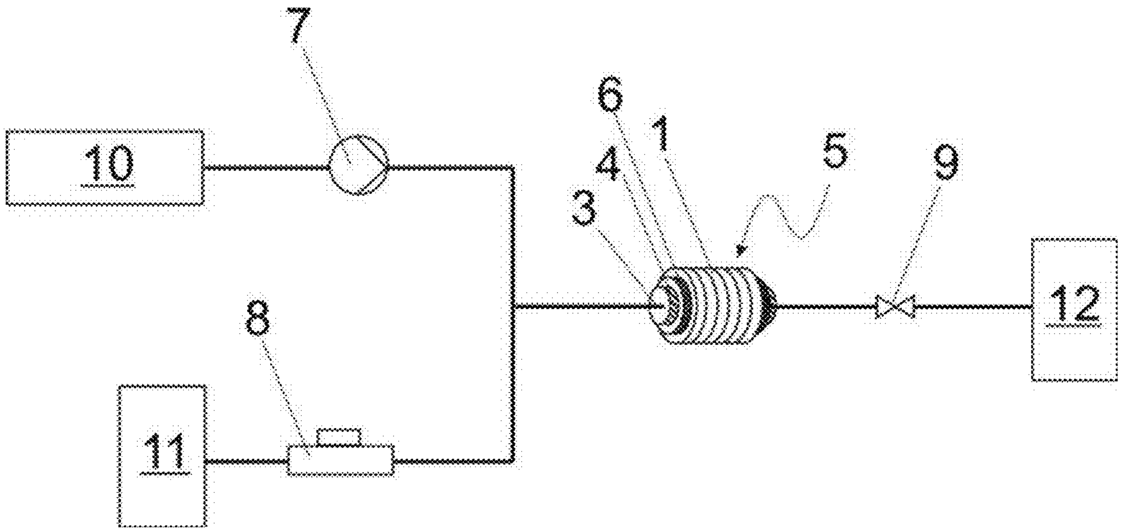

FIG. 2*a* shows a schematic representation of one of the experimental layout.

Figure 2B:
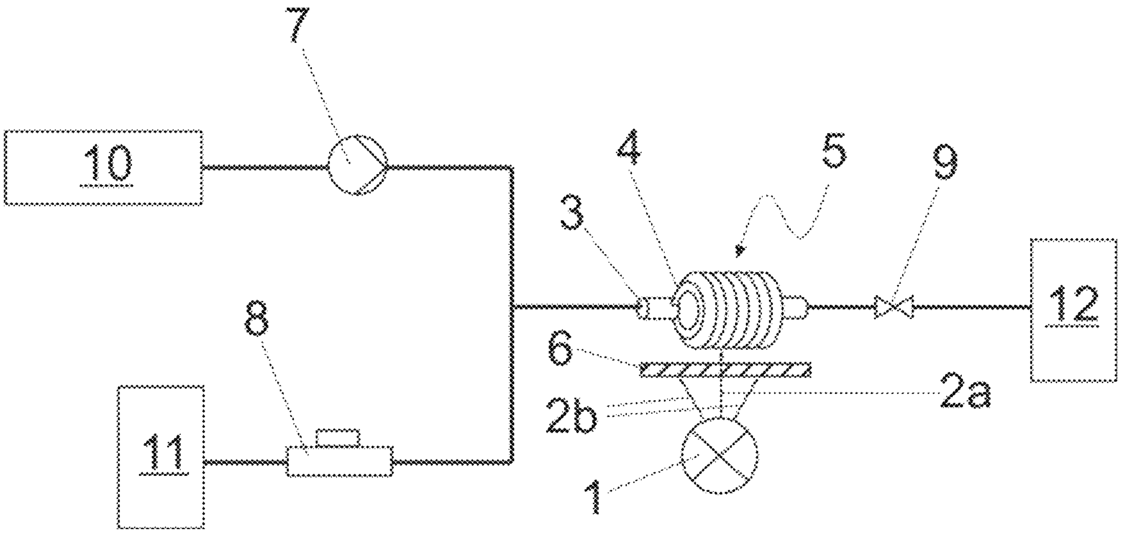

FIG. 2*b* shows a schematic representation of a different experimental layout.

Figure 2C:
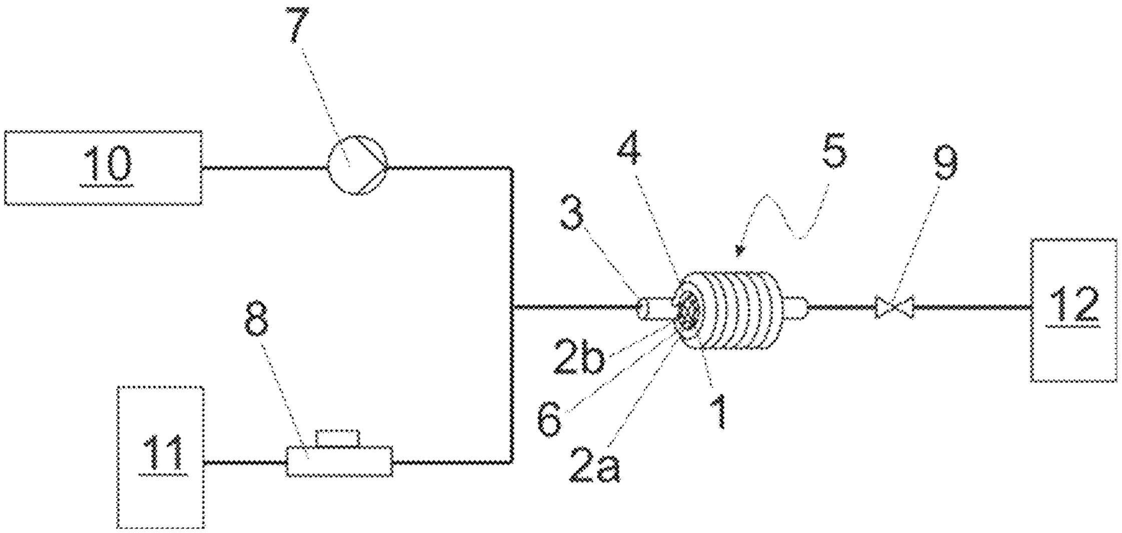

FIG. 2*c* shows a schematic representation of another different experimental layout.

Figure 3:
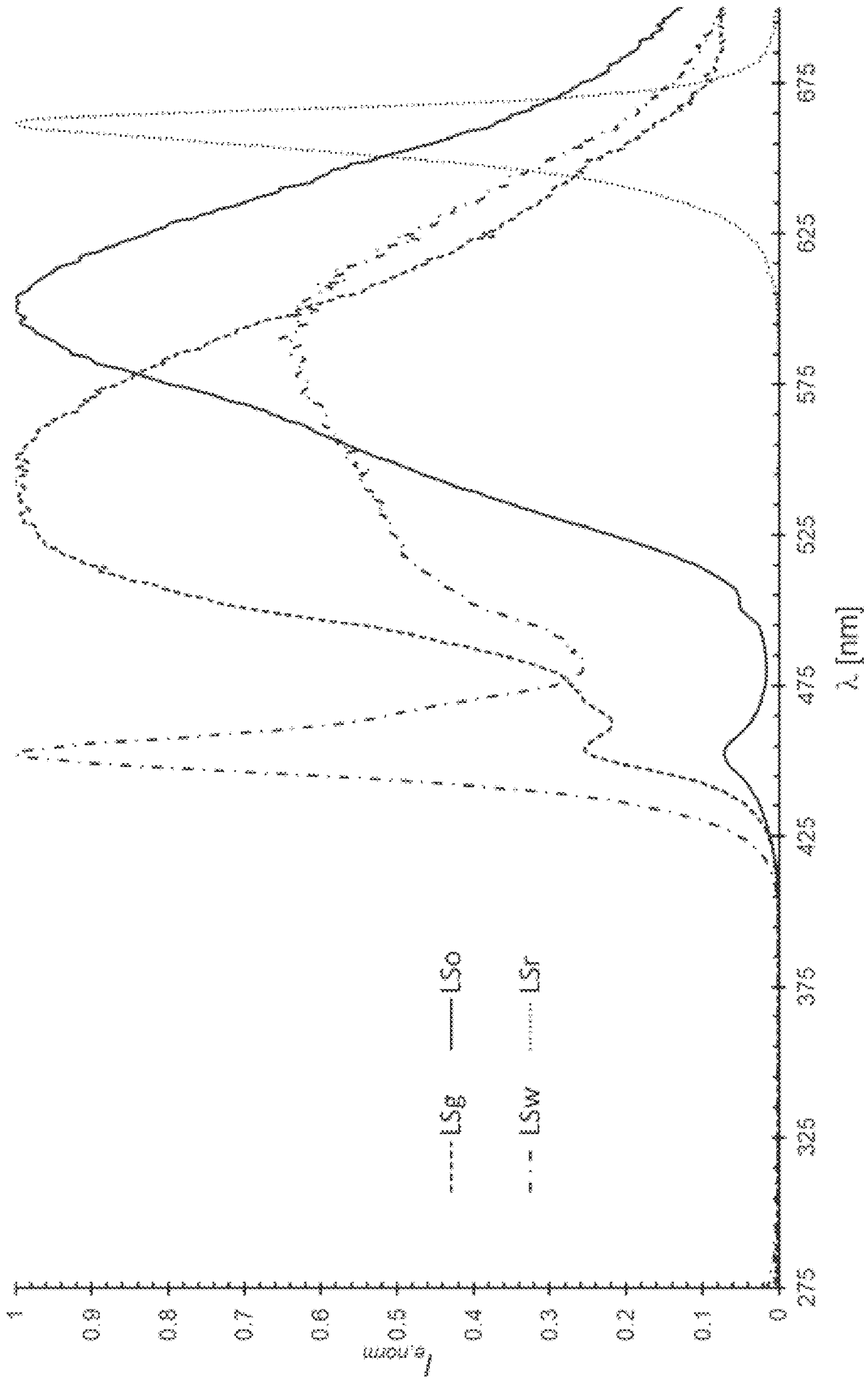

FIG. 3 represents the normalized emission spectrum of light for the photooxidation using different filter as well as of the white light and the red LED used in the experiments.

FIG. 4*a* shows a schematic representation of a continuous reactor for step b).

FIG. 4*b* shows a schematic representation of an embodiment where step b) is taken place at the end of the photoreactor of step a).

FIG. 5*a* shows a schematic representation of a continuous reactor for step c).

FIG. 5*b* shows a schematic representation of an embodiment where step c) and b) are taken place at the end of the photoreactor of step a).

FIG. 6 shows a schematic reaction scheme overview of the steps a) and b) and c).

In FIG. 2*a*, one preferred experimental layout is represented. A vessel comprising a premixture (10), comprising at least the compound of the formula (II) and the photosensitizer of the formula (III) and the solvent mixture of water and at least one $C_{1-8}$ alkanol or at least one $C_{2-4}$ alkylene diol, is pumped by a pump (7) into the photoreactor (5). Before entering the photoreactor (5), oxygen (11), preferably in the form of air, is admixed to the premixture forming the photooxidation reaction mixture (3). The amount of oxygen admixed is controlled by a mass flow controller (8). Around the transparent wall (4) of the linear tubular photoreactor (5) the light source (1) is arranged, particularly in a helical arrangement of LEDs. The light source (1) is in one embodiment a white LED. Between the transparent wall (4) and the light source (1) a filter (6) is positioned, allowing to provide a light (2*a*) which has a peak wavelength ($\lambda_{max}$) in its spectrum in the range of between 580 and 780 nm. The filter (6) is particularly an orange filter or an red filter, respectively, to provide particularly a light which has a peak wavelength ($\lambda_{max}$) in its spectrum in the range of between 585 and 625 nm or 625 and 740 nm, respectively. The light source (1) is in another preferred embodiment either an orange LED or a red LED, particularly a red LED, in the case of which the filter (6) is not present. The photoreactor (5) is preferably a spiral flow reactor. At the outlet of the photoreactor a backpressure regulator (9) is positioned before the product is collected in the collection vessel (12).

This experimental layout, particularly the combination of light source and photoreactor, is preferably used for higher volume photoreactions.

In FIG. 2*b*, another preferred experimental layout is represented. A vessel comprising a premixture (10), comprising at least the compound of the formula (II) and the photosensitizer of the formula (III) and the solvent mixture of water and at least one $C_{1-8}$ alkanol or at least one $C_{2-4}$ alkylene diol, is pumped by a pump (7) into the photoreactor (5). Before entering the photoreactor (5), oxygen (11) is admixed to the premixture forming the photooxidation reaction mixture (3). The amount of oxygen admixed is controlled by a mass flow controller (8).

The light source (1) is in one embodiment a white LED. Between the transparent wall (4) of the photoreactor (5) and the light source (1), a filter (6) is positioned, allowing to provide a light (2*a*) which has a peak wavelength ($\lambda_{max}$) in its spectrum in the range of between 580 and 780 nm. In the present representation only one light source (1) and one filter (6) is shown. It is, of course, possible that several such light sources (1), combined with the filter (6) are positioned around the photoreactor (5), in the form of a spiral flow reactor, can be positioned to allow an even irradiation of the whole photoreactor (5). The filter (6) is particularly an orange filter or an red filter, respectively, to provide particularly a light which has a peak wavelength ($\lambda_{max}$) in its spectrum in the range of between 585 and 625 nm or 625 and 740 nm, respectively. The light having undesired wavelengths (2*b*) is filtered off by the filter (6). The light source (1) is in other preferred embodiment either an orange LED or a red LED, more preferably a red LED, in the case of which the filter (6) is not present. At the outlet of the photoreactor a backpressure regulator (9) is positioned before the product is finally collected in the collection vessel (12).

This experimental layout, particularly the combination of light source and photoreactor, is preferably used for smaller volume photoreactions.

In FIG. 2*c*, another preferred experimental layout is represented. A vessel comprising a premixture (10), comprising at least the compound of the formula (II) and the photosensitizer of the formula (III) and the solvent mixture of water and at least one $C_{1-8}$ alkanol or at least one $C_{2-4}$ alkylene diol, is pumped by a pump (7) into the photoreactor (5). Before entering the photoreactor (5), oxygen (11), preferably in the form of air, is admixed to the premixture forming the photooxidation reaction mixture (3). The amount of oxygen admixed is controlled by a mass flow controller (8).

In this embodiment a light source (1), preferably a red LED, is arranged in the hollow space formed by the helical windings of the spiral flow reactor (5).

The light source (1) is in one embodiment a white LED. Around the light source (1), i.e. between the transparent wall (4) of the photoreactor (5) and the light source (1), a filter (6) is positioned, allowing to provide a light (2*a*) which has a peak wavelength ($\lambda_{max}$) in its spectrum in the range of between 580 and 780 nm. The filter (6) is particularly an orange filter or an red filter, preferably a red filter, respectively, to provide particularly a light which has a peak wavelength ($\lambda_{max}$) in its spectrum in the range of between 585 and 625 nm or 625 and 740 nm, respectively. The light having undesired wavelengths (2*b*) is filtered off by the filter (6). The light source (1) is in other preferred embodiment either an orange LED or a red LED, preferably a red LED, in the case of which the filter (6) is not present. At the outlet of the photoreactor a backpressure regulator (9) is positioned before the product is finally collected in the collection vessel (12).

This experimental layout, particularly the combination of light source and photoreactor, is preferably used for smaller volume photoreactions.

In an even further embodiment the light source (1) and filter (6) of FIGS. 2*b*) and 2*c*) are combined. In other words the filter and light source can be arranged outside of the photoreactor walls arranged inside as well as outside of the space formed by the helical winding of the spiral flow photoreactor (5).

In FIG. 4*a*, a preferred experimental layout of the reaction step b) of is shown allowing the reduction of compound of the formula (I) to be performed in a continuous way. The compound of formula (I) (13) is transferred by means of a pump (7) into the reactor for reduction (14) to which also the reducing agent (15) is added by a pump (7). In a variation to this, the adding of the compound of formula (I) and reducing agent is realized before the entering of compound of the formula (I) into reactor (14). In case further ingredients (not shown in FIG. 4*a*) are used for the reduction, said additional ingredients may be added either to the reducing agent (15) or to the compound of the formula (I) (13) or separately fed into the reduction reactor (14). In the reactor for reduction (14) the compound of the formula (I) is reduced to the compound of the formula (IV) which is transferred from the reactor to the collection vessel (12) for the compound of the formula (IV).

In FIG. 4*b*, a more preferred experimental layout of the reaction steps a) and b) is shown allowing the photoreaction of mesitol and the reduction of compound of the formula (I) to be performed both in a continuous way. In the embodiment shown corresponds basically the combination of representation shown in FIG. 2*c* and FIG. 4*a*. In this embodiment, however, the compound of the formula (I) is transferred from the outlet of the photoreactor (5) directly to the entry of the reactor for the reduction of compound of the formula (I) to the compound of the formula (IV).

In FIG. 5*a*, a preferred experimental layout of the reaction step c) is shown. The compound of formula (IV) (16) is transferred by means of a pump (7) into the reactor for thermal treatment (17) to which also the basic substance (18) is added by a pump (7). In a variation to this, the adding of the compound of formula (IV) and basic substance is realized before the entering of compound of the formula (IV) into reactor (17). In case further ingredients (not shown in FIG. 5*a*) are used for the thermal treatment, said additional ingredients may be added either to the basic substance (18) or to the compound of the formula (IV) (16) or separately fed into the reactor for thermal treatment (17).

In the reactor for thermal treatment (17) the compound of the formula (IV) is transformed to the compound of the formula (V) which is transferred from the reactor to the collection vessel (12) for the compound of the formula (V).

In FIG. 5*b*, a more preferred experimental layout of the reaction steps a) and b) and c) is shown allowing the photoreaction of mesitol and the reduction of compound of the formula (I) and the thermal treatment of the compound of the formula (IV) to be performed all in a continuous way. In the embodiment shown corresponds basically the combination of representation shown in FIG. 4*b* and FIG. 5*a*. In this embodiment, however, the compound of the formula (IV) is transferred from the outlet of the reduction reactor (14) directly to the entry of the reactor for the thermal treatment of compound of the formula (IV to the compound of the formula (V).

LIST OF REFERENCE SIGNS

1 Light source
2*a* Light of desired wavelength
2*b* Light of undesired wavelength
3 Photooxidation reaction mixture
4 Transparent wall of photoreactor
5 Photoreactor
6 Filter
7 Pump
8 Mass flow controller
9 Backpressure regulator
10 Premixture
11 Oxygen
12 Collection vessel
13 Compound of formula (I)
14 Reactor for reduction
15 Reducing agent
16 Compound of formula (IV)

17 Reactor for thermal treatment
18 Basic substance

EXAMPLES

The present invention is further illustrated by the following experiments.

Example 1: Photooxidation of 2,4,6-trimethylphenol (Step a)

In the following experiment an experimental layout has been used as schematically represented in FIG. 2*c:*

A vessel comprising a premixture (10) of solvent, respectively solvent mixture and the substances to be photooxidized as well as the photosensitizer is pumped by a pump (7) into the photoreactor (5) which is a spiral flow reactor. Before entering the photoreactor (5), oxygen in the form of air (11) is admixed to the premixture forming the photooxidation reaction mixture (3). The amount of air admixed is controlled by a mass flow controller (8). The light of the light source (1) is red LED (12×OSLON® SSL Hyper red, $\lambda_{max}$=660 nm, ca. 9 W & 700 lm for 12 LED, GH CSSPM1.24, 120° viewing angle, CPU cooling system (10 V) to maintain ambient temperature (ca. 20° C.)) (no filter is used) (see spectrum shown as LSr in FIG. 3) so that the light of the desired wavelengths (2*a*) is falling on the transparent walls (4) of the photoreactor (5). The photoreactor (5) is coiled over an inner glass cylinder around a LED lamp (1) cooled with a fan. At the outlet of the photoreactor a backpressure regulator (9) is positioned before the product is finally collected in the collection vessel (12).

More precisely, the photooxidation has been performed as followed:

A solution of 2,4,6-trimethylphenol (20.0 mmol·$L^{-1}$, 2.00 mmol [for the duration of the reaction], 1.0 eq.) and methylene blue hydrate (0.180 nmol, 0.900 mol % [CAS: 122965-43-9]) in methanol and water (4:1, v/v) is prepared to give a homogenous blue solution. The solution is pumped through a high-pressure liquid chromatography pump (Dionex P580) into the photoreactor (tubing system: 0.75 mm internal diameter, 1.58 mm outer diameter, PFA coil) (liquid flow rate: 0.093 m L/m in, HPLC regulated piston pump) with a constant pressure of 10 bar (regulated by back pressure regulator, Equilibar Zero-Flow ZF1 back pressure regulator, computer controlled).

Before entering the photoreactor, the solution is enriched with air (air flow rate: 0.500 mL/min, mass flow controller, Bronkhorst EI-FLOW, Modell: FG—200CV-AAD-22-K-DA-000 S/N: M19209993A). Inside the photoreactor, the reaction mixture is exposed to a red LED light source (12×OSLON® SSL Hyper red, $\lambda_{max}$=660 nm, ca. 15 W & 700 lm for 12 LED, GH CSSPM1.24, 120° viewing angle) (see spectrum shown as LSr in FIG. 3) during a residence time of 40 minutes. Complete conversion confirmed by thin layer chromatography (4:1 Cyclohexane/EtOAc, $R_f$(substrate)=0.63, $R_f$(product)=0.3). The photoreactor is kept at ambient temperature (20° C.) by 2 vans (one inside the photoreactor: CPU cooling system, one outside the photoreactor: regular van). The reaction mixture (100 mL) is collected by a 250 mL round bottom flask equipped with a septum and a needle outlet to prevent overpressure. Methanol is removed under reduced pressure until constant residual amount (15 mbar). Water (50 mL) is added to the residue and the solution is extracted with ethyl acetate (3×50 mL). The combined organic layers are washed with brine (50 mL), dried over $Na_2SO_4$, filtered and the organic solvent is removed under reduced pressure (15 mbar) to yield 4-hydroperoxy-2,4,6-trimethylcyclohexa-2,5-dien-1-one as a green-greyish viscous wax (340 mg, 99% yield).

Example 2: Reduction of 4-hydroperoxy-2,4,6-trimethylcyclohexa-2,5-dien-1-one (Step b)

In a 50 mL round bottom flask a yellow solution of 4-hydroperoxy-2,4,6-trimethylcyclohexa-2,5-dien-1-one (300 mg, 1.78 mmol, 1.0 eq.), as prepared by example 1, and sodium thiosulfate (1.40 g, 8.90 mmol, 5.0 eq.) in methanol and water (25 mL, 4:1 v/v) is prepared. The reaction mixture is stirred at ambient temperature until complete conversion monitored by thin layer chromatography (4:1 cyclohexane/EtOAc, $R_f$(substrate)=0.3, $R_f$(product)=0.2). A color change of the solution from yellow to pink is observed. Methanol is removed under reduced pressure. Water (30 mL) is added to the residue and the solution is extracted with ethyl acetate (3×25 mL). The combined organic layers are washed with brine (30 mL), dried over $Na_2SO_4$, filtered and the organic solvent is removed under reduced pressure (15 mbar) to yield 4-hydroxy-2,4,6-trimethylcyclohexa-2,5-dien-1-one as a yellow green viscous wax (253 mg, 93% yield).

Example 3: Formation of 2,3,5-trimethylhydroquinone (Step c)

In the following experiment an experimental layout has been used as schematically represented in FIG. 5*a:*

A solution of 4-hydroxy-2,4,6-trimethyl-2,5-cyclohexadien-1-one (4.7 g, 30 mmol), as obtained by example 2, in an aqueous NaOH solution (440 ml, 0.008 mol/l), methanol (50 ml) and sodium sulphite (235 mg, 1.9 mmol) was pumped through a flow reactor (diameter 1.5 mm, length: 2000 mm) with 10 ml/min at 250° C. The solution was neutralized at the end of the flow reactor with sulfuric acid (1.47 ml). The reaction mixture was extracted with ethyl acetate, dried over $MgSO_4$, and concentrated in vacuo. 2,3,5-trimethylbenzoquinone (4.45 g, 95%) was obtained in 92% yield.

The invention claimed is:

1. A process for manufacturing a compound of formula (I) from a compound of formula (II):

(I)

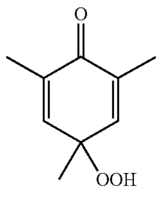

(II)

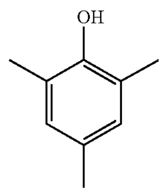

wherein the process comprises:

conducting photooxidation of the compound of formula (II) using oxygen and a photosensitizer of the formula (III):

(III)

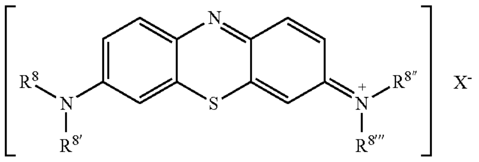

wherein $R^8$, $R^{8'}$, $R^{8''}$ and $R^{8'''}$ independently from each other represent either a H, or a $C_{1-4}$ alkyl group; or wherein $R^8$ and $R^{8'}$ and/or $R^{8''}$ and $R^{8'''}$ form together with N a five or six membered ring;

with the proviso that at least one of the residues $R^8$, $R^{8'}$, $R^{8''}$ and $R^{8'''}$ is different from H; and $X^-$ represents an anion;

in a solvent mixture of water and at least one $C_{1-8}$ alkanol or at least one $C_{2-4}$ alkylene diol; and wherein the photooxidation is conducted using light which has a peak wavelength ($\lambda_{max}$) in a spectrum of the light which is in a range of between 580 and 780 nm.

2. The process according to claim 1, wherein the light used for the photooxidation has a peak wavelength ($\lambda_{max}$) in the spectrum in the range of between 625 and 740 nm.

3. The process according to claim 1, wherein more than 80% of the light has a wavelength of between 525 and 780 nm.

4. The process according to claim 1, wherein the solvent mixture is a mixture of water and at least one alcohol selected from the group consisting of methanol, ethanol and isopropanol.

5. The process according to claim 1, wherein the light is emitted from a light source which is a red LED lamp.

6. The process according to claim 1, wherein the light is emitted from a light source which is a white LED lamp in combination with a filter which blocks wavelengths below 500 nm.

7. The process according to claim 1, wherein $R^8=R^{8'}=R^{8''}=R^{8'''}=CH_3$.

8. The process according to claim 1, wherein $X^-$ is halide.

9. The process according to claim 1, wherein at the beginning of the photooxidation, the compound of the formula (II) is present in a concentration in a range of between 0.002 to 2.0 mol/l.

10. The process according to claim 1, wherein the compounds of formulas (II) and (III) are present in a ratio of the compound of the formula (III) to the compound of the formula (II) which is in a range of between 0.005 and 20 mol %.

11. The process according to claim 1, wherein the process is a continuous process.

12. The process according to claim 1, wherein more than 80% of the light has a wavelength of between 525 and 700 nm.

13. The process according to claim 1, wherein the light is emitted from a light source which is a white LED lamp in combination with a filter which blocks wavelengths below 625 nm.

14. The process according to claim 1, wherein $X^-$ is chloride.

15. The process according to claim 1, wherein at the beginning of the photooxidation, the compound of the formula (II) is present in a concentration in the range of between 0.01 to 0.2 mol/l.

16. The process according to claim 1, wherein the compounds of formulas (II) and (III) are present in a ratio of the compound of the formula (III) to the compound of the formula (II) which is in a range of between 0.05 and 20 mol %.

17. The process according to claim 1, wherein the compounds of formulas (II) and (III) are present in a ratio of the compound of formula (III) to the compound of formula (II) which is in a range of between 0.2 and 10 mol %.

18. A process for preparing a compound of formula (IV):

(IV)

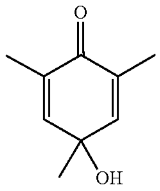

, wherein the process comprises the steps of:

a) conducting the photooxidation according to claim 1 to form the compound of formula (I) from the compound of formula (II); and b) bringing the compound of formula (I) into contact with a reducing agent to reduce the compound of formula (I) and yield the compound of formula (IV).

19. The process according to claim 18, wherein step b) is performed continuously.

20. A process for preparing a compound of formula (V):

(V)

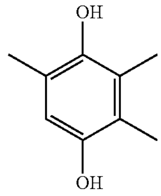

, wherein the process comprises the steps of:

a) conducting the photooxidation according to claim 1 to form the compound of formula (I) from the compound of formula (II);

b) bringing the compound of formula (I) into contact with a reducing agent to reduce the compound of formula (I) and yield a compound of formula (IV):

(IV)

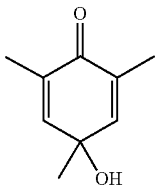

, c) treating the compound of formula (IV) with a basic substance at a temperature of >200° C. to yield the compound of formula (V).

21. The process according to claim 20, wherein step c) is practiced by treating the compound of formula (IV) with a basic substance at a temperature of >240° C. to yield the compound of formula (V).

22. The process according to claim 20, wherein steps b) and/or c) are performed continuously.

* * * * *